United States Patent [19]

Ziman

[11] 4,230,711
[45] Oct. 28, 1980

[54] FUNGICIDAL N-SUBSTITUTED 4,4-DIALKYL HOMOPHTHALIMIDES

[75] Inventor: Stephen D. Ziman, San Francisco, Calif.

[73] Assignee: Chevron Research Company, San Francisco, Calif.

[21] Appl. No.: 8,200

[22] Filed: Jan. 31, 1979

[51] Int. Cl.$^2$ .................... A61K 31/47; C07D 217/24
[52] U.S. Cl. ..................................... 424/258; 546/142
[58] Field of Search ........................ 546/142; 424/258

[56] References Cited

U.S. PATENT DOCUMENTS

| 2,553,770 | 5/1951 | Kittleson | 424/274 |
| 3,178,447 | 4/1965 | Kohn | 548/311 |
| 3,886,163 | 5/1975 | Kadin | 546/142 |
| 4,179,508 | 12/1979 | Austel et al. | 424/258 |

FOREIGN PATENT DOCUMENTS 2011126  3/1970  Fed. Rep. of Germany ........... 546/142

OTHER PUBLICATIONS

Harriman et al., J. A. C. S. 67, 1481–1482 (1945).

Primary Examiner—Glennon H. Hollrah
Assistant Examiner—David E. Wheeler
Attorney, Agent, or Firm—D. A. Newell; T. G. DeJonghe; R. J. Suyat

[57] ABSTRACT

Compounds of the formula

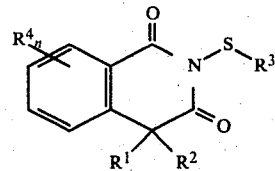

wherein $R^1$ and $R^2$ are independently alkyl groups containing 1 to 6 carbon atoms; $R^3$ is a haloalkyl group of the formula $C_mY_{(m-1)}X_{(m+2)}$ wherein X is fluoro, chloro, bromo or iodo and m=1 or 2; Y is hydrogen, fluoro, chloro, bromo or iodo; $R^4$ is hydrogen, an alkyl group containing 1 to 6 carbon atoms, alkoxy containing 1 to 6 carbon atoms, alkenyl containing 2 to 6 carbon atoms, nitro, hydroxy, alkoxyalkyl containing 2 to 6 carbon atoms, fluoro, bromo, chloro or iodo and n—1, 2, 3 or 4, have fungicidal activity.

10 Claims, No Drawings

FUNGICIDAL N-SUBSTITUTED 4,4-DIALKYL HOMOPHTHALIMIDES

BACKGROUND OF THE INVENTION

The present invention relates to certain N-alkylthio homophthalimides and their use as fungicides.

It has now been found that certain N-alkylthio homophthalimides are effective for fungicidal applications, particularly leaf blights caused by *Phytophthora infestans, Septoria apii, Alternaria solari* and *Erysiphe polygoni.* Thus, the compounds of the invention are useful for protecting commercial crops from harmful fungi.

Harriman et al. disclose in *J. Am. Chem. Soc.,* 67, 1481-2 (1945) N-alkyl-substituted homophthalimides having no apparent hypnotic activity.

U.S. Pat. No. 3,178,447 discloses N-(1,1,2,2-tetrachloroethylthio)phthalimide having fungicidal activity.

U.S. Pat. No. 2,553,770 discloses N-(trichloromethylthio)phthalimide having fungicidal activity.

SUMMARY OF THE INVENTION

Among other factors, the present invention is based on my finding that while 4,4-dialkyl homophthalimides exhibit virtually no fungicidal activity, their N-(haloalkylthio) derivatives are fungicidal.

DESCRIPTION OF THE INVENTION

This invention relates to compounds represented by the formula

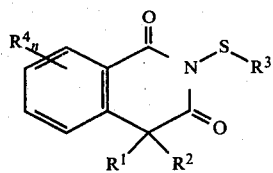

wherein $R^1$ and $R^2$ are independently alkyl groups containing 1 to 6 carbon atoms; $R^3$ is a haloalkyl group of the formula $C_mY_{(m-1)}X_{(m+2)}$ wherein X is fluoro, chloro, bromo or iodo and $m=1$ or 2; Y is hydrogen, fluoro, chloro, bromo or iodo; $R^4$ is hydrogen, an alkyl group containing 1 to 6 carbon atoms, alkoxy containing 1 to 6 carbon atoms, alkenyl containing 2 to 6 carbon atoms, nitro, hydroxy, alkoxyalkyl containing 2 to 6 carbon atoms, fluoro, bromo, chloro or iodo, and $n=1$, 2, 3 or 4.

Preferred groups for $R^1$ and $R^2$ are methyl and ethyl. Most preferably $R^1$ and $R^2$ are both methyl.

Preferably, $R^3$ is trifluoromethyl or 1,1,2,2-tetrachloroethyl.

Representative groups for $R^4$ are hydrogen, methyl, ethyl, methoxy, nitro, methoxymethyl, fluoro, bromo, chloro or iodo. Most preferably $R^4$ is hydrogen when $n=4$. When $R^4$ is other than hydrogen, n is preferably 1.

The compounds of the invention are made by reacting substantially equimolar amounts of a 4,4-dialkyl homophthalimide and a base, preferably triethylamine, and thereafter adding an equivalent of a haloalkyl sulfenyl chloride. The reaction is carried out in a dry, inert organic solvent, preferably methylene chloride, at ambient room temperature. The reaction can also be carried out with sodium hydride as the base and tetrahydrofuran as solvent.

The 4,4-dialkyl homophthalimides can be obtained by alkylating a 4-alkyl homophthalimide or dialkylating a homophthalimide according to conventional alpha-alkylation procedures, e.g. by sequential reaction with a base, such as sodium hydroxide, and an alkyl iodide. Homophthalimides are known in the literature and generally are prepared from homophthalic acids.

Alternatively, 4,4-dialkylhomophthalimides may be prepared from benzenes or a substituted benzene according to the following scheme:

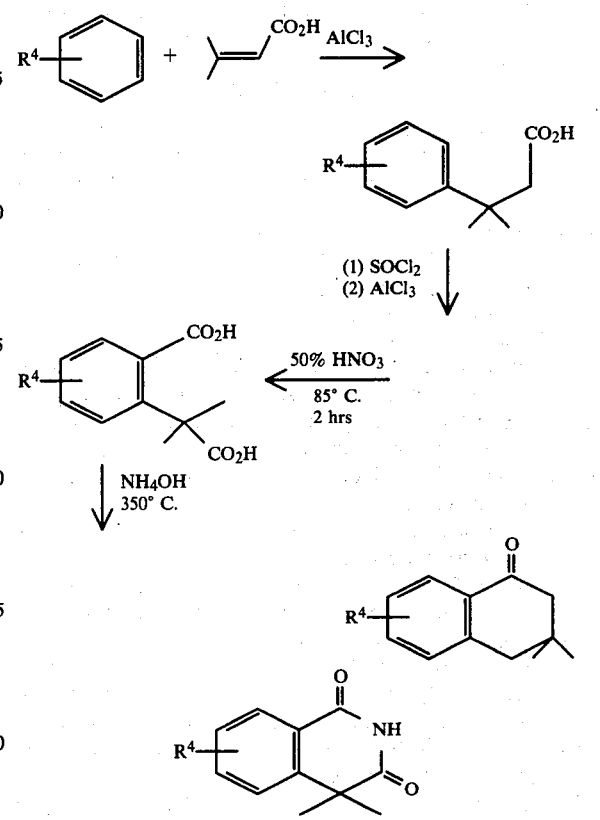

The compounds of the invention have been found useful for controlling fungi, particularly plant fungal infections caused by leaf blights caused by organisms such as *Phytophthora infestans, Septoria apii, Alternaria solari* and *Erysiphe polygoni.*

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5–80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant. Useful liquid concentrates include the emulsifiable concentrates which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant growth regulators, fertilizers, etc.

EXAMPLES

EXAMPLE 1—Preparation of homophthalimide

Homophthalic acid (150 g) was mixed with 200 ml concentrated (28%) ammonium hydroxide and the mixture was heated to distill off water and form the bisammonium salt. The mixture was then heated to approximately 350° C., evolving ammonia and water, and kept at 300° C. for 20 minutes.

The crude mixture was recrystallized in acetic acid, filtered, washed with ethanol, ether and methylene chloride, dried in vacuum. Yield 67 g, m.p. 224°–7° C.

EXAMPLE 2—Preparation of 4,4-dimethyl homophthalimide

To 63 g homophthalimide in 600 ml ethanol was added a solution of 31.3 g sodium hydroxide in 80 ml water. The mixture was stirred and heated to reflux. Methyl iodide (111.1 g) was added dropwise and the mixture was allowed to reflux overnight. The ethanol was stripped off and the residue was redissolved in chloroform and washed with water. The chloroform layer was stripped and the residue purified by chromatography to give 14.2 g solid crystalline product, m.p. 103°–105° C.

EXAMPLE 3—Preparation of N-(trichloromethylthio)-4,4-dimethyl homophthalimide To 4,4-dimethyl homophthalimide (5.6 g) in 200 ml dry tetrahydrofuran was added 1.73 g sodium hydride. The mixture was stirred for one hour, then 5.75 g (3.38 ml) trichloromethyl sulfenyl chloride was added dropwise. The mixture was refluxed overnight, stripped of solvent, slurried in hexane and decanted. The brown crystalline residue was purified by tlc and recrystallized in ethanol to yield 3.2 g of the brown crystalline product, m.p. 129°–130° C.

EXAMPLE 4—Preparation of N-(1,1,2,2-tetrachloroethylthio)-4,4-dimethyl homophthalimide To a 200-ml methylene solution of 4,4-dimethylhomophthalimide (33.5 g) and 1,1,2,2-tetrachloroethyl sulfenyl chloride (42.2 g) at 0° C. was added dropwise 18.2 g triethylamine over 5 minutes. The mixture was stirred for 4 hours, washed with 200 ml water and dried (MgSO4). The solvent was evaporated and a brown oil was recovered, recrystallized in ethanol to yield 54 g (78%) tan solid, m.p. 112°–113° C.

EXAMPLE 5—Tomato Late Blight

Compounds of the invention were tested for the control of the Tomato Late Blight organism *Phytophthora infestans conidia*. Six- to seven-week-old tomato (variety Bonny Best) seedlings were used. The tomato plants were sprayed with a 250-ppm solution of the test compound in acetone, water and a small amount of a nonionic emulsifier. The sprayed plants were then inoculated one day later with the organism, placed in an environmental chamber and incubated at 19°–20° C. and 100% relative humidity for at least 16 hours. Following the incubation, the plants were allowed to dry and then were maintained at 60–80% relative humidity for approximately 7 days. The percent disease control provided by a given test compound was based on the percent disease reduction relative to the untreated check plants. The compounds giving effective control at the test concentration are tabulated in Table I.

EXAMPLE 6—Tomato Early Blight

Compounds of the invention were tested for the control of the Tomato Early Blight organism, *Alternaria solani conidia*. Tomato (variety Bonny Best) seedlings of 6 to 7 weeks old were used. The tomato plans were sprayed with a 250-ppm solution of the test compound in an acetone-and-water solution containing a small amount of a non-ionic emulsifier. The sprayed plants were inoculated one day layer with the organism, dried and maintained at 60–80% relative humidity for about 12 days. Percent disease control was based on the percent disease development on untreated check plants. The compounds giving effective control at the test concentrated are tabulated in Table I.

EXAMPLE 7—Celery Late Blight

Compounds of the invention were tested for the control of Celery Late Blight using celery (Utah) plants 12 to 14 weeks old. The Celery Late Blight organism was *Septoria apii*. The celery plants were sprayed with solutions of the candidate toxicant mixed with acetone, water and a nonionic emulsifier. The plants were then inoculated with the organism and placed in an environmental chamber and incubated at 19°–20° C. in 100% relative humidity for an extended period of time (approximately 48 hours). Following the incubation, the plants were allowed to dry and then were maintained at a 60–80% relative humidity for approximately 14 days. The percent disease control provided by a given candidate toxicant is based on the percent disease reduction relative to untreated check plants. The compounds giving effective control at the test concentrations are reported in Table I.

EXAMPLE 8—Powdery Mildew

The powdery mildew test was made using bean seedlings (var. Bountiful), 2 weeks old, with well-developed primary leaves. The pathogen was *Erysiphe polygoni*. The bean seedlings were sprayed with a 250-ppm solution of the test compound in an acetone-water mixture containing a non-ionic emulsifier. The treated plants were inoculated one day after spray application of the test compound with the pathogen. The plants were then maintained in a greenhouse at a 60–80% relative humidity and at a temperature of 19°–20° C. The rate of infection on the leaves was made after about 10 days. The percent disease control provided by a given test compound was based on the disease reduction relative to untreated check plants. The compounds of the invention giving effective control at the test concentrations are reported in Table I.

TABLE I

|  | Compound 1 % Control @ 250 ppm | Compound 2 % Control @ 250 ppm | Compound 3 % Control @ 250 ppm |
|---|---|---|---|
| Tomato Late Blight | 95 | 50 | 0 |
| Tomato Early Blight | 33 | 73 | 0 |
| Celery Late Blight | 50 | — | 0 |
| Bean Powdery Mildew | 96 | 0 | 0 |

1 = N-(trichloromethyl)thio-4,4-dimethyl homophthalimide
2 = N-(1,1,2,2-tetrachloroethyl)thio-4,4-dimethyl homophthalimide
3 = 4,4-dimethyl homophthalimide
A figure of 100% represents maximum fungicidal effectiveness at the given concentration.

What is claimed is:

1. A compound of the formula

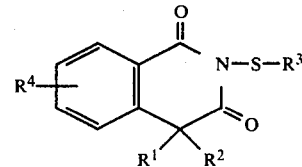

wherein $R^1$ and $R^2$ are independently alkyl groups of 1 to 6 carbon atoms; $R^3$ is a haloalkyl group of the formula $C_m Y_{(m-1)} X_{(m+2)}$ wherein X is fluoro, chloro, bromo or iodo and $m=1$ or 2; Y is hydrogen, fluoro, chloro, bromo or iodo; $R^4$ is hydrogen, an alkyl group of 1 to 6 carbon atoms, alkoxy of 1 to 6 carbon atoms, alkenyl of 2 to 6 carbon atoms, nitro, hydroxy, alkoxyalkyl of 2 to 6 carbon atoms, fluoro, bromo, chloro or iodo.

2. A compound according to claim 1 wherein $R^4$ is hydrogen.

3. A compound according to claim 1 wherein $R^1$ and $R^2$ are methyl.

4. A compound according to claim 3 wherein $R^4$ is hydrogen.

5. A compound according to claim 4 wherein $R^3$ is trichloromethyl.

6. A compound according to claim 4 wherein $R^3$ is 1,1,2,2-tetrachloroethyl.

7. A fungicidal composition comprising a fungicidally effective amount of a compound defined in claim 1 and a biologically inert carrier.

8. A method for the control of fungi which comprises contacting said fungi or their habitats with a fungicidally effective amount of a compound defined in claim 1.

9. A method for controlling *Phytophthora infestans* fungi which comprises applying to said fungi or their habitats a fungicidally effective amount of a compound defined in claim 1.

10. A method for controlling *Erysiphe polygoni* fungi which comprises applying to said fungi or their habitats a fungicidally effective amount of a compound defined in claim 1.

* * * * *